(12) United States Patent
Pressman et al.

(10) Patent No.: US 7,863,463 B2
(45) Date of Patent: Jan. 4, 2011

(54) METHOD OF PURIFYING DIANHYDRIDES

(75) Inventors: Eric James Pressman, East Greenbush, NY (US); Albert Santo Stella, Voorheesville, NY (US); Beatriz Peñalver Bernabe, Evansville, IN (US); Lioba Maria Kloppenburg, Mt. Vernon, IN (US); Lee Harris Bergman, Houston, TX (US)

(73) Assignee: Sabic Innovative Plastics IP B.V. (NL)

( * ) Notice: Subject to any disclaimer, the term of this patent is extended or adjusted under 35 U.S.C. 154(b) by 1297 days.

(21) Appl. No.: 11/286,190

(22) Filed: Nov. 22, 2005

(65) Prior Publication Data

US 2007/0117990 A1 May 24, 2007

(51) Int. Cl.
*C07D 307/77* (2006.01)
(52) U.S. Cl. ....................................... 549/241
(58) Field of Classification Search ............. 549/241
See application file for complete search history.

(56) References Cited

U.S. PATENT DOCUMENTS

| | | | |
|---|---|---|---|
| 1,301,388 A | 4/1919 | Conover et al. | |
| 2,786,805 A | 3/1957 | Sullivan et al. | |
| 2,937,189 A | 5/1960 | Hoffman et al. | |
| 2,985,665 A | 5/1961 | Lawn et al. | |
| 3,236,885 A | 2/1966 | Gray | |
| 3,338,923 A | 8/1967 | Peterlein | |
| 4,870,194 A | 9/1989 | Molinaro et al. | 549/241 |
| 4,906,760 A | 3/1990 | Mueller et al. | |
| 4,914,231 A | 4/1990 | Manami et al. | 562/429 |
| 5,145,971 A | 9/1992 | Lesins | |
| 5,229,482 A | 7/1993 | Brunelle | 528/125 |
| 5,336,788 A | 8/1994 | Lesins | 549/250 |
| 7,495,113 B2 * | 2/2009 | Pressman et al. | 549/239 |

FOREIGN PATENT DOCUMENTS

| | | |
|---|---|---|
| EP | 0264624 | 4/1988 |
| EP | 0 421 046 | 6/1995 |
| EP | 1674443 | 6/2006 |
| GB | 0 823 507 | 11/1959 |

OTHER PUBLICATIONS

Johnson et al., "Method to Prepare Bis(Haloimides)", U.S. Appl. No. 11/022,907, filed Dec. 22, 2004.
Silva et al., "Method for the Preparation of Bis(Haloimides)", U.S. Appl. No. 11/232,285, filed Sep. 21, 2005.

\* cited by examiner

*Primary Examiner*—Janet L Andres
*Assistant Examiner*—David E Gallis
(74) *Attorney, Agent, or Firm*—Cantor Colburn LLP

(57) ABSTRACT

Disclosed herein is a method for purification of dianhydrides comprising a substantial amount (10000 ppm or more) of at least one metal salt. In one aspect the method is useful for the purification of dianhydrides prepared by the reaction of a halophthalic anhydride with a metal carbonate and may be optionally catalyzed by a phase transfer catalyst. The purification of the dianhydrides may be accomplished by hydrolyzing the dianhydride metal salt mixture directly to a tetraacid with an inorganic acid, followed by separating the impurities from an aqueous phase, and subsequently heating the tetraacid to effect ring closure to form a purified dianhydride having less than 50 parts per million metal halide and lower levels of other residual impurities. In one aspect the method is highly effective in removing phase transfer catalyst impurities such as hexalkylguanidinium halides initially present in the dianhydride undergoing purification.

21 Claims, No Drawings

US 7,863,463 B2

METHOD OF PURIFYING DIANHYDRIDES

BACKGROUND

This invention relates to a method for preparing a purified dianhydride. In one aspect the invention relates to purification of oxydiphthalic anhydrides.

Dianhydrides are often prepared from the halogen derivatives of a suitable monoanhydride, for example, by coupling two molecules of a suitable haloanhydride using a coupling reagent. The crude product of such a coupling reaction often includes organic solvents, unreacted starting material(s), catalysts, ionic substances, metal salt by-products, and various color bodies and the like.

Many processes for the purification of anhydrides and dianhydrides are known. For example, processes for the purification of phthalic anhydride and pyromellitic acid are disclosed in U.S. Pat. Nos. 1,301,388; 2,937,189; 2,985,665; and 3,236,885. U.S. Pat. No. 2,786,805 discloses the purification of phthalic anhydride. U.S. Pat. No. 3,338,923 discloses purifying pyromellitic dianhydride. U.S. Pat. No. 4,870,194, discloses the purification of oxydiphthalic anhydride.

U.S. Pat. No. 4,906,760 discloses removal of metal ion impurities from aromatic anhydrides by heating the anhydride to be purified in an aqueous solution, treating the solution with activated carbon, filtering off the carbon, cooling and crystallizing a purified aromatic acid corresponding to the anhydride being purified. In this same vein, U.S. Pat. No. 4,906,760 discloses the removal of metal ion impurities from an aromatic anhydride by hydrolysis of the anhydride in aqueous solution, treatment with activated carbon and recovering an aromatic polyacid.

British Patent, GB 823,507, discloses that tetrachlorophthalic anhydride can be purified by dissolving it in water containing 2-20% of a water miscible ether. The crude tetrachlorophthalic anhydride is dissolved in a mixture of water and the ether and then filtered hot.

U.S. Pat. No. 4,914,231 discloses a method for purifying diphenylsulfone tetracarboxylic acids by dissolving the crude dianhydride in a mixture of water and acetic acid to generate the crude tetracarboxylic acid and allowing the acid to crystallize. European Patent No. 0421 046 A1 discloses a process for producing highly pure 3,3',4,4'-biphenyltetracarboxylic acid and the corresponding anhydride. The anhydride to be purified is treated with hot water at a temperature of 95° C. to 105° C. The impurities dissolve in the water and the anhydride is converted to the corresponding tetraacid.

U.S. Pat. No. 5,145,971 discloses a process for the preparation of purified oxydiphthalic acid from impure oxydiphthalic anhydride, by treating the impure dianhydride with a mixture of water and propionic acid or butyric acid to produce the corresponding tetraacid, oxydiphthalic acid. The tetraacid may be converted to oxydiphthalic anhydride via known methods, for example as disclosed in U.S. Pat. No. 5,336,788.

Despite numerous disclosed methods for the purification of anhydrides and dianhydrides there is a continuing need to develop improved processes for the purification and isolation of dianhydrides. It would be desirable therefore to provide new and more efficient methods for preparing purified dianhydrides.

BRIEF DESCRIPTION

In one aspect, the invention provides a method of preparing a purified dianhydride, said method comprising:
  (a) providing a first mixture comprising: an organic solvent, a dianhydride, and at least 10,000 parts per million of a metal halide salt relative to the total weight of the dianhydride;
  (b) combining the first mixture with water and at least one inorganic acid to form a second mixture;
  (c) heating said second mixture until substantially all of said dianhydride is converted to a tetraacid formed as an ingredient in a third mixture, said third mixture comprising an organic layer and an aqueous layer;
  (d) subjecting the third mixture to at least one operation selected from the group consisting of:
    (i) removing substantially all of the organic solvent to produce an aqueous slurry of the tetraacid;
    (ii) removing the organic layer from the aqueous layer to form a mixture comprising the tetraacid and the organic solvent; and
    (iii) filtering to form a tetraacid wet cake; and
  (e) subjecting the product formed in step (d) to at least one operation selected from the group consisting of:
    (iv) filtering to provide a tetraacid wet cake;
    (iv) combining a tetraacid wet cake with at least one organic solvent to produce a mixture comprising a tetraacid and an organic solvent; and
    (vi) effecting ring closure of a tetraacid ingredient;

to provide a purified dianhydride comprising less than 50 parts per million of said metal halide salt.

In another aspect, the invention provides a method of preparing a purified dianhydride, said method comprising:
  (a) providing a first mixture comprising: an organic solvent, a dianhydride, and at least 10,000 parts per million of a metal halide salt relative to the weight of the dianhydride;
  (b) filtering the first mixture to form a first mixture as a solid mass comprising the dianhydride, metal halide salt, and residual organic solvent;
  (c) combining the filtered first mixture with water and at least one inorganic acid to form a second mixture;
  (d) heating said second mixture until substantially all of said dianhydride is converted to a tetraacid formed as an ingredient in a third mixture;
  (e) subjecting the third mixture to the following operations:
    (i) removing substantially all of the residual organic solvent to produce an aqueous slurry of the tetraacid; and
    (ii) filtering to form a tetraacid wet cake,
    (iii) combining the tetraacid wet cake with at least one organic solvent to produce a fourth mixture comprising the tetraacid and a solvent; and
    (iv) effecting ring closure in said tetraacid ingredient of the fourth mixture;

to provide a purified dianhydride comprising less than 50 parts per million of said metal halide salt.

In yet another aspect, the invention provides a method of preparing a purified oxydiphthalic anhydride, said method comprising:
  (a) providing a first mixture comprising: an organic solvent, an oxydiphthalic anhydride, and at least 10,000 parts per million of a metal halide salt relative to the total weight of the oxydiphthalic anhydride;
  (b) combining the first mixture with water and at least one inorganic acid to form a second mixture;
  (c) heating said second mixture until substantially all of said oxydiphthalic anhydride is converted to a tetraacid formed as an ingredient in a third mixture, said third mixture comprising an organic layer and an aqueous layer;

(d) subjecting the third mixture to at least one operation selected from the group consisting of:
  (i) removing substantially all of the organic solvent to produce an aqueous slurry of the tetraacid;
  (ii) removing the organic layer from the aqueous layer to form a mixture comprising the tetraacid and the organic solvent; and
  (iii) filtering to form a tetraacid wet cake;

(e) subjecting the product formed in step (d) to at least one operation selected from the group consisting of:
  (iv) filtering to form a tetraacid wet cake;
  (v) combining a tetraacid wet cake with at least one organic solvent to produce a mixture comprising a tetraacid and an organic solvent; and
  (vi) effecting ring closure in said tetraacid ingredient of a mixture comprising a tetraacid and an organic solvent;

to provide a purified oxydiphthalic anhydride comprising less than 50 parts per million of said metal halide salt.

In yet another further aspect, the invention provides a method of preparing a purified dianhydride, said method comprising:

(a) providing a first mixture comprising: an organic solvent, a dianhydride, and at least 10,000 parts per million of a metal halide salt relative to the total weight of the dianhydride;

(b) combining the first mixture with water and at least one inorganic acid to form a second mixture;

(c) heating said second mixture until substantially all of said dianhydride is converted to a tetraacid formed as an ingredient in a third mixture, said third mixture comprising an organic layer and an aqueous layer;

(d) subjecting the third mixture to at least one operation selected from the group consisting of:
  (i) removing substantially all of the organic solvent to produce an aqueous slurry of the tetraacid;
  (ii) removing the organic layer from the aqueous layer to form a mixture comprising the tetraacid and the organic solvent; and
  (iii) filtering to form a tetraacid wet cake; and (e) subjecting the product formed in step (d) to at least one operation selected from the group consisting of:
  (iv) filtering to provide a tetraacid wet cake;
  (v) combining a tetraacid wet cake with at least one organic solvent to produce a mixture comprising a tetraacid and an organic solvent; and
  (vi) effecting ring closure in said tetraacid ingredient of a mixture comprising a tetraacid and an organic solvent;

to provide a purified dianhydride comprising less than 50 parts per million of said metal halide salt.

In a further aspect, the invention provides a method of preparing a polymer, said method comprising (A) preparing a purified dianhydride by:
  (a) providing a first mixture comprising: an organic solvent, a dianhydride, and at least 10,000 parts per million of a metal halide salt relative to the weight of the dianhydride;
  (b) combining the first mixture with water and at least one inorganic acid to form a second mixture;
  (c) heating said second mixture until substantially all of said dianhydride is converted to a tetraacid formed as an ingredient in a third mixture; said third mixture comprising an organic layer and an aqueous layer;
  (d) subjecting the third mixture to at least one operation selected from the group consisting of:
    (i) removing substantially all of the organic solvent to produce an aqueous slurry of the tetraacid;
    (ii) removing the organic layer from the aqueous layer to form a mixture comprising the tetraacid and the organic solvent; and
    (iii) filtering to form a tetraacid wet cake; and
  (e) subjecting the product formed in step (d) to at least one operation selected from the group consisting of:
    (iv) filtering to provide a tetraacid wet cake;
    (v) combining a tetraacid wet cake with at least one organic solvent to produce a mixture comprising a tetraacid and an organic solvent; and
    (vi) effecting ring closure in said tetraacid ingredient of a mixture comprising a tetraacid and an organic solvent;

to provide a purified dianhydride comprising less than 50 parts per million of said metal halide salt; and (B) polymerizing the purified dianhydride with a comonomer to form a polymer.

DETAILED DESCRIPTION

The present invention may be understood more readily by reference to the following detailed description of preferred embodiments of the invention and the examples included herein. In this specification and in the claims which follow, reference will be made to a number of terms which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "polymeric species" includes both polymeric and oligomeric materials. Polymeric materials are defined as having weight average molecular weights, $M_w$, greater than 15,000 daltons, and oligomeric materials are defined as having weight average molecular weights, $M_w$, less than 15,000 daltons.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having $4n+2$ "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC(CF$_3$)$_2$PhO—), 4-chloromethylphen-1-yl, 3-trifluorovinyl-2-thienyl, 3-trichloromethylphen-1-yl (i.e., 3-CCl$_3$Ph—), 4-(3-bromoprop-1-yl)phen-1-yl (i.e., 4-BrCH$_2$CH$_2$CH$_2$Ph—), and the like. Further examples of aromatic radicals include 4-allyloxyphen-1-oxy, 4-aminophen-1-yl (i.e., 4-H$_2$NPh—), 3-aminocarbonylphen-1-yl (i.e., NH$_2$COPh—), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph—), 4-mercaptomethylphen-1-yl (i.e., 4-HSCH$_2$Ph—), 4-methylthiophen-1-yl (i.e., 4-CH$_3$SPh—), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis (phenyl), and the like. The term "a $C_3$-$C_{10}$ aromatic radical" includes aromatic radicals containing at least three but no more than 10 carbon atoms. The aromatic radical 1-imidazolyl (C$_3$H$_2$N$_2$—) represents a $C_3$ aromatic radical. The benzyl radical (C$_7$H$_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group (C$_6$H$_{11}$CH$_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis (cyclohex-4-yl) (i.e., —C$_6$H$_{10}$C(CF$_3$)$_2$C$_6$H$_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., CH$_3$CHBrCH$_2$C$_6$H$_{10}$O—), and the like. Further examples of cycloaliphatic radicals include 4-allyloxycyclohex-1-yl, 4-aminocyclohex-1-yl (i.e., H$_2$NC$_6$H$_{10}$—), 4-aminocarbonylcyclopent-1-yl (i.e., NH$_2$COC$_5$H$_8$—), 4-acetyloxycyclohex-1-yl, 2,2-dicyanoisopropylidenebis(cyclohex-4-yloxy) (i.e., —OC$_6$H$_{10}$C(CN)$_2$C$_6$H$_{10}$O—), 3-methylcyclohex-1-yl, methylenebis(cyclohex-4-yloxy) (i.e., —OC$_6$H$_{10}$CH$_2$C$_6$H$_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —OC$_6$H$_{10}$(CH$_2$)$_6$C$_6$H$_{10}$O—), 4-hydroxymethylcyclohex-1-yl (i.e., 4-HOCH$_2$C$_6$H$_{10}$—), 4-mercaptomethylcyclohex-1-yl (i.e., 4-HSCH$_2$C$_6$H$_{10}$—), 4-methylthiocyclohex-1-yl (i.e., 4-CH$_3$SC$_6$H$_{10}$—), 4-methoxycyclohex-1-yl, 2-methoxycarbonylcyclohex-1-yloxy (2-CH$_3$OCOC$_6$H$_{10}$O—), 4-nitromethylcyclohex-1-yl (i.e., NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g., (CH$_3$O)$_3$SiCH$_2$CH$_2$C$_6$H$_{10}$—), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl (C$_4$H$_7$O—) represents a $C_4$ cycloaliphatic radical. The cyclohexylmethyl radical (C$_6$H$_{11}$CH$_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e., —CHO), hexyl, hexamethylene, hydroxymethyl (i.e., —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilylpropyl (i.e., (CH$_3$O)$_3$SiCH$_2$CH$_2$CH$_2$—), vinyl, vinylidene, and the like. By way of further example, a $C_1$-$C_{10}$ aliphatic radical contains at least one but no more than 10 carbon atoms. A methyl group (i.e., CH₃—) is an example of a $C_1$ aliphatic radical. A decyl group (i.e., CH₃(CH₂)₉—) is an example of a $C_{10}$ aliphatic radical.

As noted, in one embodiment, the invention provides a method of preparing a purified dianhydride, said method comprising:

(a) providing a first mixture comprising: an organic solvent, a dianhydride, and at least 10,000 parts per million of a metal halide salt relative to the total weight of the dianhydride;

(b) combining the first mixture with water and at least one inorganic acid to form a second mixture;

(c) heating said second mixture until substantially all of said dianhydride is converted to a tetraacid formed as an ingredient in a third mixture, said third mixture comprising an organic layer and an aqueous layer;

(d) subjecting the third mixture to at least one operation selected from the group consisting of:
  (i) removing substantially all of the organic solvent to produce an aqueous slurry of the tetraacid;
  (ii) removing the organic layer from the aqueous layer to form a mixture comprising the tetraacid and the organic solvent; and
  (iii) filtering to form a tetraacid wet cake; and (e) subjecting the product formed in step (d) to at least one operation selected from the group consisting of:
  (iv) filtering to provide a tetraacid wet cake;
  (v) combining a tetraacid wet cake with at least one organic solvent to produce a mixture comprising a tetraacid and an organic solvent; and
  (vi) effecting ring closure in said tetraacid ingredient of a mixture comprising a tetraacid and an organic solvent;

to provide a purified dianhydride comprising less than 50 parts per million of said metal halide salt.

Typically, the dianhydride to be purified is selected from the group of dianhydrides represented by structure I

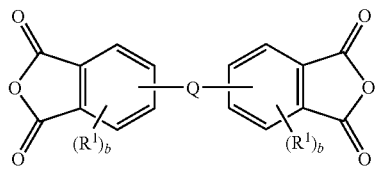

I wherein Q is a bond, an oxygen atom, a sulfur atom, a sulfinyl group, a sulfonyl group, a selenium atom, a hexafluoroisopropylidene group, a $C_1$-$C_{30}$ aliphatic radical, a $C_3$-$C_{30}$ cycloaliphatic radical, or a $C_3$-$C_{30}$ aromatic radical, or a carbonyl group; $R^1$ is a halogen atom, a nitro group, a cyano group, a $C_1$-$C_{12}$ aliphatic radical, $C_3$-$C_{12}$ cycloaliphatic radical, or a $C_3$-$C_{12}$ aromatic radical; and b is independently at each occurrence an integer from 0 to 3.

Exemplary dianhydrides falling within generic formula I which may be purified using the method of the present invention are given in Table 1.

TABLE 1

| Entry | Q | $R^1$ | $R^2$ | Structure |
|---|---|---|---|---|
| I-1 | Bond | H | H | 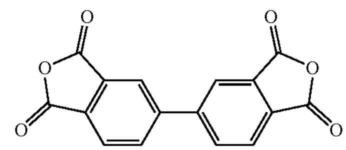 |
| I-2 | O | H | H | 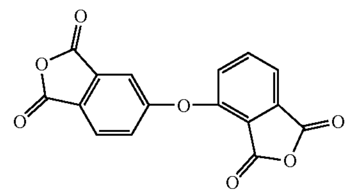 |
| I-3 | O | CN | CN | 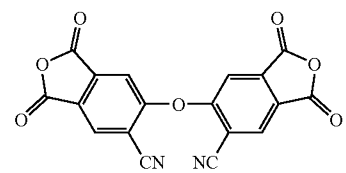 |
| I-4 | S | CH₃ | CH₃ | 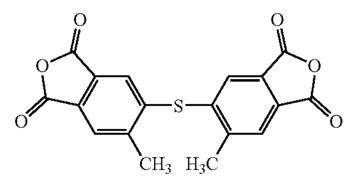 |
| I-5 | S | H | H | 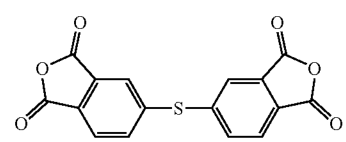 |
| I-6 | Se | H | H | 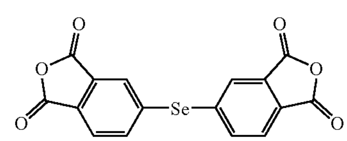 |
| I-7 | C(CF₃)₂ | H | H | 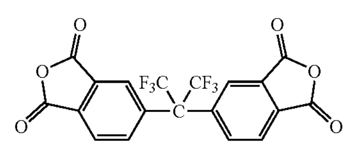 |

Entry I-1 of Table 1 illustrates the structure of 4,4'-biphenyldianhydride. Entry I-2 of Table 1 illustrates the structure of 3,4'-oxydiphthalic anhydride. Entry I-5 of Table 1 illustrates the structure 4,4'-thiodiphthalic anhydride. Entry I-6 of Table 1 illustrates the structure 4,4'-selenyldiphthalic anhydride. Entry I-7 of Table 1 illustrates the structure 4,4'-(hexafluoroisiopropylidene) diphthalic anhydride (CAS No. 1102-00-2). Other exemplary dianhydrides which may be purified using the method of the present invention include 4,4'-carbonyldiphthalic anhydride (CAS No. 2421-28-5); and 4,4'-(4,4'-isopropylidenediphenoxy)bis(phthalic anhydride) (i.e. BPADA, CAS No. 38103-06-9).

In a specific embodiment of the present invention, the dianhydride purified according to the method of the invention is 4,4'-oxydiphthalic anhydride (hereinafter sometimes referred to as "ODPA") (structure V). In an alternate specific embodiment, the dianhydride purified by the method of the present invention is 4,4'-(4,4'-isopropylidenediphenoxy)bis(phthalic anhydride) (structure VI). In an alternate embodiment the dianhydride purified by the method of the present invention comprises an isomeric mixture of oxydiphthalic anhydride, for example a mixture chiefly comprised of 4,4'-oxydiphthalic anhydride but also comprising minor amounts of the 3,3'-oxydiphthalic anhydride and 3,4'-oxydiphthalic anhydride. In an alternate embodiment, the dianhydride comprises substantial amounts of 3,3'-oxydiphthalic anhydride. In yet another embodiment, the dianhydride is 3,3'-oxydiphthalic anhydride containing less than about 1 percent of either of 3,4'-oxydiphthalic anhydride or 4,4'-oxydiphthalic anhydride.

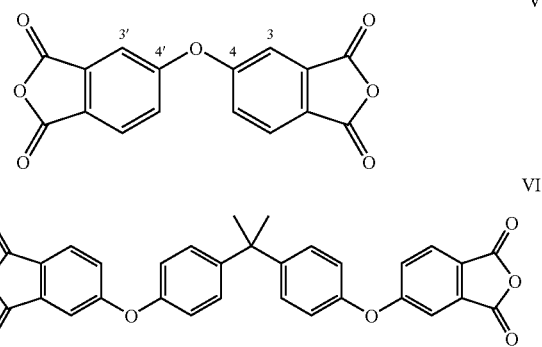

As noted, the present invention relates to the purification of dianhydrides comprising a substantial amount (at least 10,000 parts per million (ppm)) of a metal halide salt. The impure dianhydride requiring purification may encountered in a variety of situations, for example where a dianhydride comprising less than 10,000 ppm of a metal halide salt is inadvertently contacted with a metal halide contaminant. The method of the present invention is in one embodiment used to purify dianhydrides made using a "halo-displacement" process in which a stoichiometric amount of a metal halide salt is produced as a by-product. For example, dianhydride V is conveniently prepared by reaction of 4-chlorophthalic anhydride with potassium carbonate in the presence of a phase transfer catalyst in a solvent such as orthodichlorobenzene (ODCB) at elevated temperature. BPADA, compound VI, is conveniently prepared by reaction of 4-chlorophthalic anhydride with the disodium salt of bisphenol A (BPANa$_2$) in the presence of a phase transfer catalyst in a solvent such as orthodichlorobenzene (ODCB) at elevated temperature. Those skilled in the art will appreciate that in the preparation of dianhydride V or VI by the halo-displacement process just described, the product mixture may comprise substantially more than 10,000 parts per million metal halide salt as a by-product relative to the total weight of product dianhydride.

As noted, a convenient preparation of ODPA (for example compound V), relies upon a halophthalic anhydride as a starting material. Halophthalic anhydrides are known in the art and may be prepared, by, for example, halogenation of orthoxylene followed by catalytic oxidation using one of the many popular variations of the so-called "Mid-Century" process. Halophthalic anhydrides may be prepared wherein the halogen substituent occupies position 3 or position 4 of the halophthalic anhydride. It is possible, using known methods, to prepare a pure 3-halophthalic anhydride, a pure 4-halophthalic anhydride, or a mixture comprising both the 3-halophthalic anhydride and 4-halophthalic anhydride. Those skilled in the art will appreciate that reaction of pure 3-halophthalic anhydride with potassium carbonate in a solvent such as ODCB at elevated temperature in the presence of a phase transfer catalyst will provide 3,3'-oxydiphthalic anhydride. Alternatively, reaction of pure 3-halophthalic anhydride with potassium carbonate in a solvent such as ODCB at elevated temperature in the presence of a phase transfer catalyst will provide 4,4'-oxydiphthalic anhydride. Similar reaction of a mixture of 3-halophthalic anhydride and 4-halophthalic anhydride will provide a mixture of oxydiphthalic anhydrides comprising 4,4'-oxydiphthalic anhydride, 3,4'-oxydiphthalic anhydride, and 3,3'-oxydiphthalic anhydride. In each instance, a stoichiometric amount of potassium halide salt is produced as a by-product of the reaction. The halophthalic anhydride may comprise any halogen, but typically fluorine, chlorine or bromine halogen substituents are preferred. Chlorophthalic anhydride, either as a mixture of 3- and 4-chlorophthalic anhydrides, or as pure 3-chlorophthalic anhydride or pure 4-chlorophthalic anhydride is generally preferred by reason of its relatively low cost and particular suitability. Those skilled in the art will recognize that fluoro phthalic anhydride, either as a mixture of 3- and 4-fluorophthalic anhydrides, or as pure 3-fluorophthalic anhydride or pure 4-fluorophthalic anhydride may at times present special advantages owing to the greater reactivity of fluorine substituents in nucleophilic aromatic substitution reactions. In one embodiment, the purified dianhydride made by the method of the present invention consists essentially of 3,3'-oxydiphthalic anhydride. In an alternate embodiment, the purified dianhydride made by the method of the present invention consists essentially of 3,4'-oxydiphthalic anhydride. In yet another embodiment, the purified dianhydride made by the method of the present invention consists essentially of 3,4'-oxydiphthalic anhydride. In yet still another embodiment, the purified dianhydride made by the method of the present invention consists essentially of 4,4'-oxydiphthalic anhydride.

As noted, the halo displacement chemistry used to prepare valuable dianhydrides (for example ODPA) is typically carried out in the presence of at least one carbonate of the formula M$_2$CO$_3$, in which M is an alkali metal such as lithium sodium, potassium, rubidium or cesium. As noted, the halo displacement reaction results in the formation of a stoichiometric amount of metal halide salt by-product. In certain embodiments mixtures of carbonates are employed and as a consequence mixtures of metal halide salt by-products result. In certain instances it may be preferable that alkali metal carbonates be employed wherein the atomic number of the alkali metal is at least about 19.

In the preparation of oxydiphthalic anhydride, the halophthalic anhydride and the metal carbonate are typically contacted under reaction conditions designed to provide synthetically useful reaction rates but which do not consume the phase transfer catalyst employed. Generally, reaction temperatures in the range of from about 120° C. to about 250° C. are employed. In one embodiment, the reaction is conducted at one or more temperatures in the range of from about 170° C. to about 250° C. The reaction may be conducted at superatmospheric pressure, subatmospheric pressure, or at ambient pressure. The molar ratio of halophthalic anhydride to metal carbonate is typically in the range of from about 1.0:1 to about 3.0:1. In one embodiment, the molar ratio of halophthalic anhydride to metal carbonate is in the range of from about 2.04:1 to about 2.22:1.

The halo displacement reaction is advantageously performed in the presence of at least one organic solvent, but may in certain instances be conducted without solvent. Whether or not the dianhydride to be purified is prepared in a halo displacement reaction or by some other means, organic solvents suitable for use according to the present invention include alcohols, ketones, amides, aromatic solvents, esters, halogenated aromatic solvents, halogenated non-aromatic solvents, hydrocarbon solvents, ethers, and mixtures of solvents. In various embodiments suitable solvents have a boiling point above about 120° C., preferably above about 150° C. and more preferably above about 180° C. Suitable solvents of this type include, but are not limited to, orthodichlorobenzene, paradichlorobenzene, dichlorotoluene, 1,2,4-trichlorobenzene, diphenyl sulfone, phenetole, anisole, veratrole, and mixtures thereof. In one embodiment, chlorinated aromatic liquids may be employed as solvents, examples of which include, but are not limited to, orthodichlorobenzene, 2,4-dichlorotoluene and 1,2,4-trichlorobenzene. When 2,4-dichlorotoluene is employed as the solvent in the halo displacement route to a dianhydride, it is in certain instances observed that reduced reaction time and lower product decomposition result. In the case of some solvents, such as orthodichlorobenzene, the proportion of phase transfer catalyst employed in the halo displacement reaction may be increased and/or the reaction may be run at superatmospheric pressure to permit higher temperatures and higher reaction rates.

The halo displacement reaction mixture should be substantially anhydrous. In one embodiment, the total water content of the reaction mixture is less than about 20 parts per million (ppm). In another embodiment, the total water content of the reaction mixture is less than about 5 ppm. Any water present above this amount can inhibit the halo displacement reaction, irrespective of its source. Traces of water may be present in the organic reagents and catalysts employed. Traces of water may also be present in the metal carbonate. Typically, steps are taken to dry all of the reaction components before beginning the reaction. Drying can be achieved by methods known in the art. Liquid reagents and solvents can be dried by distillation and/or by contact with molecular sieves, and solid materials such as the carbonate and bicarbonate by heating in an oven, most often under vacuum.

In one embodiment of the present invention, the dianhydride to be purified comprises an organic phase transfer catalyst. The presence of an organic phase transfer catalyst in the dianhydride to be purified is frequently encountered when the dianhydride is prepared using the halo displacement process. The following discussion relates to phase transfer catalysts suitable for use in the halo displacement route to dianhydrides, and the organic phase transfer catalysts disclosed within the context of the halo displacement reaction may be regarded as typical of those present in dianhydrides which may be purified using the method of the present invention. It should be noted, however, that the phase transfer catalysts disclosed herein are merely exemplary of contaminants which may be present in the dianhydride to be purified. Further, it should be noted the method of the present invention may be employed to purify dianhydrides from any source, and is not limited to the purification of dianhydrides prepared by the halo displacement process. In the halo displacement process, a phase transfer catalyst is employed to enhance the rate of conversion of the reactants to the products. Typical examples of phase transfer catalysts include, but are not limited to, phosphazenium salts, guanidinium salts, and pyridinium salts. In one embodiment, a hexaalkylguanidinium halide or an α,ω-bis(pentaalkylguanidinium)alkane halide is used as a phase transfer catalyst. Such phase transfer catalysts are known in the art; reference is made, for example, to U.S. Pat. No. 5,229,482. Hexaethylguanidinium chloride is a particularly suitable phase transfer catalyst in the halo displacement process.

The proportion of phase transfer catalyst employed in the halo displacement process is usually in the range of from about 0.2 mole percent to about 10.0 mole percent based on halophthalic anhydride. In instances in which a guanidinium salt phase transfer catalyst is employed, optimum yield with minimum product decomposition over time is in some cases achieved when the proportion of guanidinium salt employed is in the range of from about 1.5 mole percent to about 2.5 mole percent.

As noted, the method of the present invention is practiced by providing a "first mixture" comprising an organic solvent, a dianhydride and at least one metal halide salt, said metal halide salt being present in an amount corresponding to at least 10,000 parts per million (ppm) relative to the total weight of the dianhydride present in the first mixture. Those skilled in the art will appreciate that the "first mixture" just described is typical of the crude product mixture formed in a halo displacement reaction, for example the halo displacement reaction involving the reaction of a mixture of 3-chlorophthalic anhydride and 4-chlorophthalic anhydride with potassium carbonate in orthodichlorobenzene solvent in the presence of hexaethylguanidium chloride. In one embodiment, the "first mixture" represents a crude halo displacement product mixture which is subjected to a series of steps following completion of the halo displacement reaction, said steps including cooling the crude product mixture to room temperature, and concentrating the crude product mixture whereby most of the solvent present in the crude product mixture is removed. Solvent removal techniques which may be employed include techniques known to those skilled in the art, for example, vacuum distillation, distillation at ambient pressure, rotary evaporation and the like. In another embodiment, the "first mixture" represents a crude product mixture from a halo displacement reaction which has been subjected to a filtration step. As used herein, the terms "filtration step" and "filtering" are broadly defined to include a process by which a solid dispersed in a liquid is separated from said liquid. "Filtering" and "Filtration step" may be used interchangeably and are illustrated by techniques such as sintered metal filtration, rotary filtration, vacuum filtration, suction filtration, gravity filtration, decantation, and centrifugation. Those skilled in the art will appreciate that the separation of a solid dispersed in a liquid, for example a mixture of solid 4,4'-oxydianhydride and solid potassium chloride dispersed in orthodichlorobenzene, may provide a solid comprising a substantial amount of the liquid, for example a solid mixture of 4,4'-oxydianhydride and solid potassium chloride comprising 5 percent by weight potassium chloride and 1 percent by weight orthodichlorobenzene. Thus, in one embodiment, the "first mixture" comprises an organic solvent, a dianhydride, and at least 10,000 parts per million of a metal halide salt relative to the weight of the dianhydride wherein the organic solvent is present in an amount corresponding to less than about 5 weight percent based on the total weight of the dianhydride present. In an alternate embodiment, the "first mixture" is a slurry comprising an organic solvent, a dianhydride, and at least 10,000 parts per million of a metal halide salt relative to the weight of the dianhydride wherein the organic solvent is present in an amount corresponding to more than about 25 weight percent based on the total weight of the dianhydride present. In yet another embodiment, the "first mixture" is a slurry comprising an organic solvent, a dianhydride, and at least 10,000 parts per million of a metal halide salt relative to the weight of the dianhydride wherein the organic solvent is present in an amount corresponding to more than about 100 weight percent based on the total weight of the dianhydride present.

In the various embodiments of the method of the present invention, the dianhydride is converted by hydrolysis to the corresponding tetraacid. Thus, in one embodiment, a dianhydride having structure I is converted during the course of the method to a corresponding tetraacid having structure VII

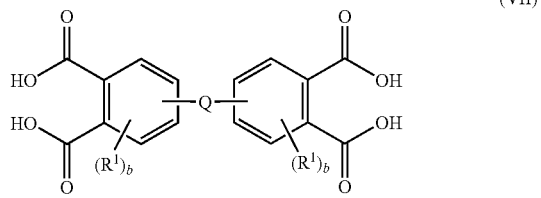

(VII)

wherein Q is a bond, an oxygen atom, a sulfur atom, a sulfinyl group, a sulfonyl group, a selenium atom, a hexafluoroisopropylidene group, a $C_1$-$C_{30}$ aliphatic radical, a $C_3$-$C_{30}$ cycloaliphatic radical, or a $C_3$-$C_{30}$ aromatic radical, or a carbonyl group; $R^1$ is a halogen atom, a nitro group, a cyano group, a $C_1$-$C_{12}$ aliphatic radical, $C_3$-$C_{12}$ cycloaliphatic radical, or a $C_3$-$C_{12}$ aromatic radical; and b is independently at each occurrence an integer from 0 to 3. In one embodiment an oxydiphthalic dianhydride is converted to an oxydiphthalic acid (hereinafter also known as "ODTA"). For example, 4,4'-oxydiphtahlic anhydride is converted to the corresponding tetraacid, 4,4'-oxydiphtahlic acid.

In one embodiment of the present invention, the "first mixture" comprising an organic solvent, a dianhydride, and at least 10,000 parts per million of a metal halide salt relative to the total weight of the dianhydride is combined with water and at least one inorganic acid to form a second mixture. The water is employed in an amount sufficient to hydrolyze completely the dianhydride to the corresponding tetraacid and to dissolve any solid metal halide salt present. Typically, water is added in an amount which is substantially in excess of the amount of water needed to effect complete hydrolysis of the dianhydride and dissolution of the metal halide salt. In one embodiment, the amount of water employed is equal to about 25 percent of the total volume of the first mixture. In another embodiment, the amount of water employed is equal to about 100 percent of the total volume of the first mixture. In yet another embodiment, the amount of water employed is equal to about 1000 percent of the total volume of the first mixture. The inorganic acid may be any inorganic acid which is soluble in water and which is effective at promoting the hydrolysis of the dianhydride to the corresponding tetraacid. In one embodiment of the present invention, the inorganic acid comprises at least one acid selected from the group consisting of boric acid, phosphoric acid, phosphorous acid, oxy acids of phosphorous, hydrochloric acid, hydrobromic acid, hydroiodic acid, sulfuric acid, and sulfurous acid. For the purposes of this application, carbonic acid is defined herein as an inorganic acid. In one embodiment, therefore, the inorganic acid is carbonic acid. In one embodiment, the inorganic acid consists essentially of carbonic acid. In another embodiment, the inorganic acid consists essentially of phosphoric acid. In yet another embodiment, the inorganic acid consists essentially of hydrochloric acid. In yet another embodiment, the inorganic acid consists essentially of hydrochloric acid. In yet still another embodiment, the inorganic acid is selected from the group consisting of carbonic acid and phosphoric acid. The inorganic acid may be added to a first mixture comprising a dianhydride as an aqueous solution. The water and the inorganic acid may be added to the first mixture in any order to form a second mixture comprising all of the components of the first mixture plus the water and inorganic acid components. The amount of inorganic acid used is typically in a range about 100 mole percent to about 500 mole percent with respect to the dianhydride but higher and lower amounts of acid may be employed.

The second mixture may then be stirred with or without heating to effect the conversion of the dianhydride to the corresponding tetraacid, but typically heating the second mixture to effect hydrolysis of the dianhydride and dissolution of the metal halide salt is preferred since reaction rates are higher and the time required for the step is correspondingly reduced. Typically, the second mixture is heated at a temperature in a range from about 30° C. to about 180° C. In one embodiment, the second mixture is heated at a temperature in a range from about 60° C. to about 160° C. In an alternate embodiment, the second mixture is heated at a temperature in a range from about 100° C. to about 130° C. In another embodiment, the second mixture is heated to the reflux temperature of water under the prevailing conditions. Further, the heating may be conducted under an inert atmosphere, such as an atmosphere of nitrogen, or argon. The heating of the second mixture may be carried out at supraatmospheric pressure. In one embodiment, the heating of the second mixture is carried out at a pressure in a range between about 1 bar and about 10 bar, preferably between about 3 bar and about 5 bar. The act of heating the second mixture for a suitable period of time, the time required to convert substantially all of the dianhydride to the corresponding tetraacid effectively converts the second mixture into a "third mixture" comprising the tetraacid, the organic solvent, the metal halide salt, water, and the inorganic acid. In one embodiment, for example when a substantial amount of the organic solvent is present, the third mixture comprises an "organic layer" and an "aqueous layer". The tetraacid is, in some embodiments, relatively insoluble in either of the organic layer or the aqueous layer of the third mixture and in such instance, the tetraacid is present as a solid dispersed in the third mixture. Those skilled in the art will appreciate that depending on the relative densities of the organic layer and the aqueous layer the aqueous layer may be disposed "on top" of the organic layer, or "below" the organic layer. In certain instances, the boundary between the layers may be indistinct, as for example, where the organic layer and aqueous layer tend to form an emulsion. In one embodiment, the third mixture comprises an organic layer and an aqueous layer, said organic layer comprising the organic solvent and said aqueous layer comprising the dissolved metal halide salt, and wherein the tetraacid is present said third mixture as a solid. In an alternate embodiment, the third mixture comprises an organic layer and an aqueous layer, said organic layer comprising the organic solvent and said aqueous layer comprising the dissolved metal halide salt, and wherein the tetraacid is dissolved in the organic layer. Those skilled in the art will appreciate that phrase "wherein the tetraacid is dissolved in the organic layer" will understand that embodiments exist embodiment in which only a portion of the total amount of tetraacid present in the third mixture is dissolved in the organic layer. In one embodiment of the present invention, as in the case in which the amount of solvent present in the third mixture is minimal, the "organic layer" referred to may be comprised almost entirely of the tetraacid. Such a condition might occur, for example, when the second mixture comprises a minimal amount of solvent, as would be the case when the first mixture, as noted, "first mixture" comprises an organic solvent, a dianhydride, and at least 10,000 parts per million of a metal halide salt relative to the weight of the dianhydride wherein the organic solvent is present in an amount corresponding to less than about 5 weight percent based on the total weight of the dianhydride present.

The third mixture is then subjected to at least one operation selected from the following operations:
(i) removing substantially all of the organic solvent to produce an aqueous slurry of the tetraacid;
(ii) removing the organic layer from the aqueous layer to form a mixture comprising the tetraacid and the organic solvent; and
(iii) filtering to form a tetraacid wet cake.

It should be emphasized that the expression "the third mixture is then subjected to at least one operation selected from the following operations", means that the third mixture is subjected to any one of the operations (i), (ii), and (iii) and is modified by that operation. That is, the application of any one of the operations (i)-(iii) to the third mixture results in a product which differs from the third mixture. Under certain circumstances described herein, two of the operations (i), (ii) and (iii) may be applied in sequence to the third mixture, and the product of the operation of the first-applied operation on the third mixture respectively. Each of these possibilities is taken up in turn.

In the first scenario (i), the third mixture is subjected to an operation comprising "removing substantially all of the organic solvent present in the third mixture to produce an aqueous slurry of the tetraacid". By "substantially all" it is meant that approximately 99 percent of the organic solvent present in the third mixture is removed. This can be achieved by various means. In one embodiment, the organic solvent is distilled from the third mixture until substantially all of the organic solvent is removed. In an alternate embodiment, the organic solvent is azeotropically distilled from the third reaction mixture until substantially all of the organic solvent is removed. In yet another embodiment another embodiment, a heated gas such as steam or nitrogen is passed through the third mixture until substantially all of the organic solvent is removed. The aqueous slurry of the tetraacid comprises the solid tetraacid, water, the inorganic acid, and the dissolved metal halide salt. In addition, the aqueous slurry produced by the action of operation (i) "removing substantially all of the organic solvent to produce an aqueous slurry of the tetraacid" on the third mixture may also comprise an organic phase transfer catalyst, for example the hexaethylguanidinium chloride phase transfer catalyst used in the preparation of the dianhydride by the halo displacement process.

In the second scenario (ii), the third mixture is subjected to an operation comprising "removing the organic layer from the aqueous layer to form a mixture comprising the tetraacid and the organic solvent". Operation (ii) is useful in the instance in which substantial amounts of organic solvent and water are present in the third mixture, the organic layer and the aqueous layer are readily separated, and either of two conditions are met (1) the tetraacid is dissolved in the organic layer, or (2) the tetraacid is dispersed as a slurry of solid tetraacid in the organic layer. The former condition is most likely in instances in which the tetraacid readily dissolves in the organic solvent. The latter condition may occur when the tetraacid is largely insoluble in both the organic layer and the aqueous layer, and particularly when the organic layer has a density greater than that of the aqueous layer. Thus, subjecting the third mixture to the operation of "removing the organic layer from the aqueous layer to form a mixture comprising the tetraacid and the organic solvent" results in either a solution of the tetraacid in the organic solvent, or a slurry of the tetraacid in the organic solvent. Those skilled in the art will appreciate that water soluble contaminants such as the metal halide salt and typical organic phase transfer catalyst will be separated from the tetraacid along with the aqueous layer.

In the third scenario, the third mixture is subjected to an operation comprising (iii) "filtering to form a tetraacid wet cake". Operation (iii) may be carried out advantageously on the third mixture whenever the tetraacid is substantially insoluble in both the organic layer and the aqueous layer. Under such conditions, operation (iii) provides the solid tetraacid as a "wet cake". By "wet cake" it is meant the tetraacid solid comprises either both water and solvent, or water alone, or solvent alone. A wet cake comprising both water and solvent arises when a third mixture in which the tetraacid is substantially insoluble in both the aqueous layer and the organic layer is filtered to provide a tetraacid wet cake and a filtrate comprising water, the organic solvent and components of the third mixture which are soluble in either or both of the aqueous layer and the organic layer. It should be noted again that as used herein, the term "filtering" encompasses a wide variety of techniques for separating a solid from a liquid including sintered metal filtration, rotary filtration, vacuum filtration, suction filtration, gravity filtration, decantation, centrifugation, and the like.

Those skilled in the art will appreciate that the application of operation (i) "removing substantially all of the organic solvent to produce an aqueous slurry of the tetraacid" renders the subsequent application operation (ii) removing the organic layer from the aqueous layer to form a mixture comprising the tetraacid and the organic solvent a logical impossibility without an additional intervening action. It should be stressed, however, that additional intervening actions are possible however and that practices including additional intervening actions are meant to come within the scope of the instant invention. Those skilled in the art will also appreciate that operation (iii) "filtering to form a tetraacid wet cake" may always be applied to the aqueous slurry of the tetraacid produced by the application of operation (i) "removing substantially all of the organic solvent to produce an aqueous slurry of the tetraacid" to the third mixture. Further, it will be recognized that the filtering operation (iii) may be applied to a mixture comprising a slurry of the tetraacid and the organic solvent to produce a wet cake of the tetraacid. As noted, a slurry of the tetraacid in the organic solvent may result from the application of operation (ii) "removing the organic layer from the aqueous layer to form a mixture comprising the tetraacid and the organic solvent" to the third mixture.

The product resulting from the application of at least one of operations (i), (ii) and (iii) to the third mixture may be one of the following: "aqueous slurry of the tetraacid", "a mixture comprising the tetraacid and the organic solvent", or "a tetraacid wet cake". This product (referred to in original claim 1 as "the product formed in step (d)") is then subjected to at least one operation selected from the following operations:
(iv) filtering to provide a tetraacid wet cake;
(v) combining a tetraacid wet cake with at least one organic solvent to produce a mixture comprising a tetraacid and an organic solvent; and
(vi) effecting ring closure in said tetraacid ingredient of a mixture comprising a tetraacid and an organic solvent;

to provide a purified dianhydride comprising less than 50 parts per million of said metal halide salt. Under certain circumstances described herein, two of the operations (iv), (v) and (vi) may be applied in sequence. Each of these possibilities is taken up in turn.

In the first scenario, in which each of operations (iv)-(v) is carried out, the product resulting from the application of at least one of operations (i), (ii) and (iii) to the third mixture is an "aqueous slurry of the tetraacid" which may be subjected to an operation comprising "filtering to provide a tetraacid wet cake". Those skilled in the art will appreciate that the aqueous slurry formed as a product from the third mixture when subjected to a filtering step as defined herein will produce a tetraacid wet cake comprising at least a residual amount of water, and a filtrate comprising water, the dissolved metal halide salt, the inorganic acid, and other impurities such the phase transfer catalyst, for example hexaethylguanidium chloride. In one embodiment, the wet cake is washed with water to effect further purification. In an alternate embodiment, the wet cake is washed with an organic solvent. In yet another embodiment, the wet cake is washed with a mixture of water and an organic solvent, for example a mixture comprising 20 percent by weight methanol and 80 percent by weight water. The tetraacid wet cake is then subjected to at least two additional operations, namely: combining the tetraacid wet cake with at least one organic solvent to produce a mixture comprising the tetraacid and an organic solvent, and effecting ring closure of the tetraacid in the organic solvent to provide the corresponding dianhydride. The dianhydride is then separated from the organic solvent to provide a purified dianhydride comprising less than 50 parts per million of said metal halide salt. Combining the tetraacid wet cake with at least one organic solvent to produce a mixture comprising a tetraacid and an organic solvent can be carried out in conventional equipment such as a reactor equipped with a stirrer and distillation head, and a variety of organic solvents, such as those described herein may be used. In one embodiment, the organic solvent is orthodichlorobenzene. In one embodiment, the mixture comprising the tetraacid and the organic solvent is heated to a temperature above the boiling point of water to effect ring closure of the tetraacid to the corresponding dianhydride with concomitant removal of water produced as a by-product of the ring closure reaction. In certain instances, it is found advantageous to employ a relatively high boiling solvent such as orthodichlorobenzene which forms an azeotrope with water. Other ring closure techniques may also be employed, such as ring closure promoted by a chemical agent such as acetic anhydride. In one embodiment, ring closure of the tetraacid is effected in the solid state by, for example, distillation of the solvent from a mixture comprising an organic solvent and the tetraacid to provide a solid residue comprising the tetraacid which is subsequently heated in the solid state to provide the purified dianhydride. In another embodiment, a solid mixture comprising the tetraacid is heated to provide a melt from which water is removed as the tetraacid undergoes ring closure to the purified dianhydride. Those skilled in the art will appreciate that ring closure of the tetraacid to the dianhydride may occur in stages, for example, a portion of the tetracid may be converted to the corresponding dianhydride as the organic solvent is distilled from a mixture comprising an organic solvent and the tetraacid. The residue remaining following the removal by distillation of the organic solvent comprises in one embodiment a mixture comprising the tetraacid and the corresponding dianhydride, which is subsequently transformed into the purified dianhydride. In the case of ring closure using acetic anhydride, the by-product acetic acid may be removed from the reaction mixture by distillation or co-distillation with the organic solvent. As the foregoing discussion makes clear, means other than heating a mixture of the tetraacid in an organic solvent to effect ring closure to the dianhydride may be employed. Thus in one embodiment of the present invention, the product resulting from the application of at least one of operations (i), (ii) and (iii) to the third mixture is subjected to at least one operation selected from the following operations:

(iv) filtering to provide a tetraacid wet cake;
(v) combining a tetraacid wet cake with at least one organic solvent to produce a mixture comprising a tetraacid and an organic solvent; and
(vi) effecting ring closure of a tetraacid ingredient;

to provide a purified dianhydride comprising less than 50 parts per million of said metal halide salt.

The product dianhydride may be isolated by conventional techniques such as crystallization or distillation, or by a combination of such techniques, for example crystallization followed by vacuum distillation.

In the second scenario, in which operation (vi) is carried out, the product resulting from the application of at least one of operations (i), (ii) and (iii) to the third mixture is "a mixture comprising the tetraacid and the organic solvent". Those skilled in the art will appreciate that there remains only to effect ring closure of the tetraacid component of the mixture to provide the dianhydride. The techniques and principles described in the first scenario are applicable here as well.

In the third scenario, in which operations (v) and (vi) are carried out, the product resulting from the application of at least one of operations (i), (ii) and (iii) to the third mixture is "a tetraacid wet cake" which when treated as depicted for the conversion of the wet cake in the first scenario affords the purified dianhydride comprising less than 50 parts per million of said metal halide salt.

In one embodiment, the present invention provides a method for the purification of a dianhydride comprising a substantial amount of metal halide salt, the method comprising the steps (a)-(e):

(a) providing a first mixture comprising: an organic solvent, a dianhydride, and at least 10,000 parts per million of a metal halide salt relative to the weight of the dianhydride;
(b) filtering the first mixture to form a first mixture as a solid mass comprising the dianhydride, metal halide salt, and residual organic solvent;
(c) combining the filtered first mixture with water and at least one inorganic acid to form a second mixture;
(d) heating said second mixture until substantially all of said dianhydride is converted to a tetraacid formed as an ingredient in a third mixture;
(e) subjecting the third mixture to each of the following operations:
(i) removing substantially all of the residual organic solvent to produce an aqueous slurry of the tetraacid; and
(ii) filtering to form a tetraacid wet cake,
(iii) combining the tetraacid wet cake with at least one organic solvent to produce a fourth mixture comprising the tetraacid and a solvent; and
(iv) effecting ring closure in said tetraacid ingredient of the fourth mixture;

to provide a purified dianhydride comprising less than 50 parts per million of said metal halide salt. Those skilled in the art will appreciate that the principles and techniques described herein may be applied advantageously when the purification scheme involves an initial "filtration step" as in this embodiment.

In yet another embodiment of the present invention, a first mixture comprising an organic solvent, a dianhydride, and at least 10,000 parts per million of a metal halide salt relative to the total weight of the dianhydride is combined with an inorganic acid and water to afford a second mixture. The second mixture is then heated to effect hydrolysis of the dianhydride to the corresponding tetraacid contained as an ingredient of a third mixture. The third mixture is then concentrated by removing water and the organic solvent, for example by distilling off the water and organic solvent, to provide the tetraacid as a solid mass. The tetraacid as a solid mass may then be subjected to one or more purification steps such as trituration with water or a solvent comprising water. In one embodiment the tetraacid as a solid mass is slurried in water and then subjected to a filtration step to provide a tetraacid wet cake which may be converted into the purified dianhydride using the techniques described herein. The tetraacid as a solid mass (also referred to herein at times as a "concentrated cake") may be stored under suitable conditions until further use. Alternately, the concentrated cake may be dried under vacuum at room temperature or higher temperatures to obtain a tetraacid comprising reduced levels of residual solvent and water. The tetraacid component of the concentrated cake may also be induced to undergo ring closure to the corresponding dianhydride by heating and removing water.

In one embodiment, the present invention provides a purified dianhydride, prepared using a hot product mixture of a dianhydride prepared by halo displacement, the hot product mixture comprising the dianhydride, an organic solvent, an organic phase transfer catalyst, and a metal halide salt, the metal halide salt being present in an amount corresponding to at least 10,000 ppm relative to the weight of dianhydride. The hot product mixture is cooled down to a temperature of less than about 100° C. Subsequently, an aqueous inorganic acid is added with stirring. Water, in addition to that present in the aqueous inorganic acid may be added at any time (e.g. either preceding the addition of the aqueous acid or thereafter). The amount of inorganic acid used is typically from about 100 mole percent to about 500 mole percent with respect to the dianhydride. Phase separation between the organic phase and the aqueous phase may occur. The method of contact between the acid solution and the crude reaction solution can be in batch mode and/or counter-current or co-current continuous mode. Agitation and/or other mixing techniques can be utilized to enhance mass transfer between the organic and aqueous phases. As the dianhydride hydrolyzes to tetraacid, it typically remains mostly as a solid phase. As noted, the inorganic salts and phase transfer catalyst typically dissolve in the aqueous phase. The requisite time for contact of the two phases to ensure complete hydrolysis will depend on factors such as the efficiency of mass transfer, the amount of inorganic acid present, the temperature employed, and the like. Optimal contact times will be readily ascertained by those skilled in the art. Separation of the tetraacid and its conversion to the corresponding purified dianhydride may be carried out as described herein.

In one embodiment, the conversion of the tetraacid to acid to the dianhydride is carried out "in situ" in a polymerization reactor, using the techniques and principles described herein, and thereafter the purified dianhydride is polymerized in the same reactor with at least one suitable comonomer. Suitable comonomers include diamines, diols, and the like. When the comonomer comprises a diamine, almost any diamine compound may be employed and used. Such diamine compounds are known in the art; reference is made, for example, to U.S. patent application Ser. No. 11/232285, entitled "Method For the Preparation of Bis(Haloimides)", filed Sep. 21, 2004, which is incorporated herein by reference. It should be noted that with respect to the interpretation and meaning of terms in the present application, in the event of a conflict between this application and any document incorporated herein by reference, the conflict is to be resolved in favor of the definition or interpretation provided by the present application.

Typically, the diamine compound comprises at least one compound having structure II:

$$H_2N-A^1-NH_2 \qquad \text{II}$$

wherein $A^1$ is a $C_2$-$C_{20}$ divalent aliphatic radical, a $C_2$-$C_{40}$ divalent aromatic radical, or a $C_4$-$C_{20}$ divalent cycloaliphatic radical. Suitable aliphatic diamine compounds represented by structure II (i.e. $A^1$ is a $C_2$-$C_{20}$ divalent aliphatic radical) include ethylenediamine, 1,3-diaminopropane, 1,4-diaminobutane, 1,6-diaminohexane, and 1,10-diaminodecane. Suitable aromatic diamine compounds represented by structure II (i.e. $A^1$ is a $C_2$-$C_{40}$ divalent aromatic radical) include 1,4-dimainonaphthalene, 2,6-diaminonaphthalene, 4,4'-diaminobiphenyl, 2,4-diaminotoluene, 2,6-diaminotoluene, 2-methyl-4,6-diethyl-1,3-phenylenediamine, 5-methyl-4,6-diethyl-1,3-phenylenediamine, 1,3-diamino-4-isopropylbenzene, and the like. Suitable cycloaliphatic diamine compounds represented by structure II (i.e. $A^1$ is a $C_4$-$C_{20}$ divalent cycloaliphatic radical) include trans-1,2-diaminocyclopentane, trans-1,4-(bis aminomethyl)cyclohexane, and the like.

In one embodiment, the diamine compound is selected from the group consisting of 4,4'-oxydianiline (ODA, CAS Reg. No. 110-80-4), bis(4-aminophenyl)sulfone, meta-phenylenediamine, and para-phenylenediamine and mixtures thereof. In an alternate embodiment, the diamine compound is selected from the group consisting of 4,4'-oxydianiline (ODA, CAS No. 110-80-4) and bis(4-aminophenyl)sulfone. In yet another embodiment, the diamine compound is 4,4'-oxydianiline. In yet still another embodiment, the diamine compound is bis(4-aminophenyl)sulfone.

In one embodiment of the invention, the diamine compound is selected from the group represented by structures III and IV

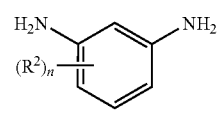

III

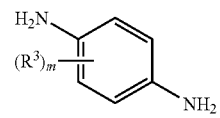

IV wherein $R^2$ and $R^3$ are independently at each occurrence a halogen atom, a nitro group, a cyano group, a $C_1$-$C_{20}$ aliphatic radical, a $C_2$-$C_{40}$ aromatic radical, or a $C_4$-$C_{20}$ divalent aliphatic radical; and "n" and "m" are independently integers ranging from 0 to 4. Examples of suitable compounds are meta-phenylenediamine, para-phenylenediamine, 2,4-diaminotoluene, 2,6-diaminotoluene, 2-methyl-4,6-diethyl-1,3-phenylenediamine, 5-methyl-4,6-diethyl-1,3-phenylenediamine, 1,3-diamino-4-isopropylbenzene, and combinations thereof.

The methods and conditions employed to polymerize the monomers are known to those skilled in the art; reference is made, for example, to U.S. patent application Ser. No. 11/232285, entitled "Method For the Preparation of Bis(Haloimides)", filed Sep. 21, 2004 and which is incorporated herein by reference. The polymerization may employ a solvent. Thus, dianhydride is contacted with at least one diamine in a solvent. Preferably the solvent is substantially water-immiscible and inert to the reaction conditions. Suitable solvents include chlorobenzene, ortho-dichlorobenzene, anisole, toluene, xylene, mesitylene, N-methyl pyrolidone, and mixtures of the foregoing solvents. In one embodiment, the polymerization is carried out under superatmospheric pressure (i.e. the pressure is greater than 1 atmosphere) and at temperatures greater than 100° C. In another embodiment, the solvent is capable of forming azeotropic mixtures with water. Orthodichlorobenzene (ODCB) is frequently the solvent of choice for the reaction.

With respect to the amounts of dianhydride and diamine employed, it is in certain embodiments preferable to have substantially equimolar amounts of the dianhydride and diamine in the reaction mixture.

In some embodiments a polymerization catalyst may be added to the polymerization reaction mixture. Suitable polymerization catalysts are known in the art. They include salts of organophosphorus acids, particularly phosphinates such as sodium phenylphosphinate (SPP) and heterocyclic amines such as 4,4'-dimethylaminopyridine (DMAP). Organic and inorganic acids may also be used to catalyze this reaction. Suitable organic acids include chlorophthalic acid, phthalic acid, and acetic acid. Sodium phenylphosphinate is a preferred catalyst in certain embodiments. The catalyst, when opted for, may be added before the diamine compound has been added, after the diamine compound has been added, or together with the diamine compound.

Polymerization is typically conducted by heating the reaction mixture to a temperature of at least 100° C., optionally in the presence of a catalyst. More typically, the reaction mixture is heated to a temperature of at least 150° C., in one embodiment in a range from about 150° C. to about 250° C., and in another embodiment in a range from about 175° C. to about 230° C. It should be noted that the reaction mixture may be heated at atmospheric pressure, subatomspheric pressure or superatmospheric pressure. When superatmospheric pressures are employed, the pressure is typically up to about 5 atmospheres, to facilitate the conversion of starting materials to polymer.

In one embodiment dianhydride is contacted with at least one diamine for a period of time sufficient to obtain the polymer of desired degree of polymerization. In a particular embodiment the contact time is for greater than about 1 hour. In one embodiment the contact time is for about 1.5 hours to about 30 hours. Appropriate contact times depend upon reaction temperatures and the nature of the reactants, and this may be determined by one skilled in the art, without undue experimentation.

EXAMPLES

The following examples are intended only to illustrate methods and embodiments in accordance with the invention, and as such should not be construed as imposing limitations upon the claims. Unless specified otherwise, all ingredients are commercially available.

Example 1

$K_2CO_3$ Drying in 10-Gallon Stainless Steel Reactor: A 10-Gallon reactor was charged with 4.5 kilograms (kg) of orthodichlorobenzene (ODCB) (PPG grade F) obtained from PPG Industries, Pittsburgh, Pa., USA. The agitator was set at low speed. While stirring, about 2.23 kg of $K_2CO_3$ (Aldrich 99% granular) was added to make a 29 weight % (wt %) slurry of $K_2CO_3$ in ODCB. The reactor was sealed and then heated to ODCB reflux (180° C.). The ODCB/water azeotrope was distilled overhead through condenser (It should be noted that water came over early in distillation). Distillation was continued until about 1.15 kg of ODCB has been removed, making a 40 wt % slurry of $K_2CO_3$ in ODCB. A sample of distillate overhead was taken and its moisture content was determined using Karl Fischer. Distillation was continued until the moisture content in overheads was less than 10 parts per million (ppm), and preferably less than 5 ppm. This amount of drying ensured that water of hydration of $K_2CO_3$ had been removed. Then, the $K_2CO_3$ slurry was drained out from the 10-Gallon reactor into collection bottles that were previously dried at 110° C. under nitrogen, under nitrogen at 55° C. with slow agitation. Each collection bottle was capped and sealed tightly with Parafilm®. About 1.5 kg of pre-dried ODCB that had been stored with dried 4A Molecular Sieves and had been treated at 200° C. under full vacuum to remove water, was used to rinse reactor contents into collection bottles.

ClPA Drying in 10-Gallon Glass-lined Reactor: A reactor was charged with about 6 kg of ODCB and 5.75 kg chlorophthalic anhydride (ClPA) obtained from Clariant Chemicals. The agitation was set at moderate level and the reactor was heated until the ODCB began to reflux (180° C.). The circulating oil temperature was set to 205° C. The ODCB/water azeotrope was distilled overhead through a condenser. The ClPA slurry was concentrated to a concentration of 61 wt % by distilling about 2.2 kg of ODCB. (It should be noted that a small amount of ClPA co-distilled with the ODCB, but the amount was negligible). A sample of distillate overhead was collected and its moisture content was determined using Karl Fischer titrator. The distillation was continued until the moisture content in overheads is less than 10 ppm, and preferably less than 5 ppm.

HEGCl/ODCB addition and drying: An addition funnel was filled with 0.992 kg of dry hexaethylguanidinium chloride (HEGCl) solution (17.1 wt % HEGCl in ODCB as measured by HPLC) and sealed. The addition funnel was attached to reactor port. The HEGCl solution was added to ClPA solution over several minutes.

$K_2CO_3$ Addition to 10-gallon Glass-Lined Reactor: The reactor and ClPA solution was maintained at about 170-175° C. (oil bypass to cool reactor slightly). A nitrogen blanket or slight positive nitrogen pressure was also maintained to protect the contents from moisture. The addition port on reactor was opened to allow the contents to be added into the reactor. The starting time for reaction was taken to be the moment when $K_2CO_3$ addition began. The $K_2CO_3$ slurry was added to the reactor under low agitation through the addition port in four approximately equal portions every 30 minutes over 2 hours. After each addition, pre-dried ODCB was used to rinse any residual slurry into reactor. The reaction port was closed, and oil flow to jacket was restarted to achieve reflux. The agitation was increased to ensure that reactor contents were thoroughly mixed. After a total of 8 hours following the initial $K_2CO_3$ addition, the conversion of ClPA to oxydiphthalic anhydride (ODPA) was complete. The reaction mixture was cooled to room temperature with stirring under nitrogen.

ODPA (Oxydiphthalic Anhydride) Purification via conversion to Oxydiphthalic tetraacid (ODTA): About 1 gram (g) of water was added to 567 g of an ODPA reaction product mixture (23 wt % ODPA by HPLC analysis; contains 133.9 grams ODPA) contained in a quart bottle at room temperature in order to coagulate the finely divided potassium chloride (potassium chloride) while minimizing hydrolysis of the anhydride. This mixture was stirred at 460 rpm for 3 minutes.

Within 1 minute, the mixture appeared to form a gel. The contents of the bottle were rinsed out of the bottle with 200 grams of ODCB and the solid ODPA suction filtered using a Buchner funnel and Whatman #2 qualitative filter paper. The filter cake was then washed with ODCB (3×325 g) and suction dried to yield 299.88 grams of a solid mixture comprising an organic solvent (orthodichlorobenzene), a dianhydride (oxydianhydride, ODPA) and a metal halide salt (potassium chloride) as a flesh colored, chunky solid which upon analysis was shown to be 44 wt % ODPA (HPLC) (corresponds to about 98% ODPA recovery). The amount of potassium chloride present (approximately 88 grams) was well in excess of 10,000 ppm based on the weight of the dianhydride present in the mixture.

The first mixture comprising ODPA-KCl-ODCB (299.88 g) was charged to a 2 liter (L), 3-necked flask equipped with a mechanical stirrer, a water cooled condenser, a nitrogen inlet, and a thermocouple-thermoregulator. To this was added 860 grams water, followed by 203 grams concentrated phosphoric acid. This corresponds to 4 moles $H_3PO_4$ per mole of ODPA. The mixture was heated to 100° C. using a heating mantle while stirring at 200 rpm. The mixture was stirred under nitrogen at about 100° C. for 13 hours. In order to remove ODCB prior to filtration of the product tetraacid, a Dean-Stark trap was introduced between the 2 L flask and the water cooled condenser. In all, about 80 grams of ODCB (essentially all of the ODCB present) was removed by distillation. The product mixture was then cooled to room temperature with stirring over 5 hours. The solid product tetraacid (ODTA) was then suction filtered on a Buchner funnel using Whatman #2 qualitative filter paper. The solid tetraacid wet cake was washed (5×250 mL) with water and suction dried to yield 193 grams of a white solid with a pink tint shown by HPLC to be 75 wt % ODTA. The wet cake was then vacuum oven dried (80° C., ~25 mm Hg, 18 hours) to yield 144.8 grams ODTA, an amount corresponding to a 95% yield from the initially charged ODPA. The product ODTA contained less than 30 ppm HEGCl, less than 0.3 wt % ODCB and was shown by ICP to contain about 35 ppm K.

Example 2

Example 2 followed a procedure nearly identical to that employed in Example 1, with the exception that 2 molar equivalents of phosphoric acid were employed in Example 2. The yield and purity of product tetraacid obtained (ODTA) were essentially the same.

As note, Example 1 and Example 2 afforded essentially equivalent results using 4 molar equivalents $H_3PO_4$ per mole of ODPA (Example 1) or using 2 molar equivalents of $H_3PO_4$ per mole of ODPA (Example 2). Additional experiments have shown that as little as 1 mole $H_3PO_4$ per mole ODPA in the hydrolysis step provides high quality ODTA at synthetically useful rates. The ODTA so produced yielded melt stable polymer following in situ ring closure to ODPA and subsequent polymerization. Failure to include an inorganic acid in the hydrolysis step, however, did not afford a purified oxydianhydride from which melt stable polymer could be prepared (See Table 2, Comparative Example 1).

TABLE 2

| Example | moles $H_3PO_4$/ mole ODPA | Impurities in isolated, purified ODTA | | |
|---|---|---|---|---|
| | | % yield | ppm HEG-Cl | ppm K(SD)* |
| Example 1 | 4 | 93 | <30 | 35(5) |
| Example 2 | 2 | 97 | <30 | 41(5) |
| Example 3 | 1 | 99 | <30 | 43(1) |
| Comparative Example 1 | 0 | 97 | <30 | 7500(100) |

*SD = standard deviation of the measurement

In scale-ups, the "filtration step" consisted of centrifugation. The ODTA-water wet cake was converted to ODPA by ring closure in ODCB, and was subsequently polymerized with or without isolation of an ODPA wet cake or dry powder.

Prophetic Examples 1-4

In the following prophetic examples, a reaction product mixture prepared in a chloro displacement reaction is subjected to the method of the present invention to provide a purified dianhydride. A reaction product mixture is obtained by reacting ClPA with $K_2CO_3$, in the presence of an organic solvent ODCB, and a phase transfer catalyst HEGCl. The reaction product mixture comprises a product ODPA, un-reacted ClPA, ODCB solvent, HEGCl phase transfer catalyst, a metal halide salt by-product (KCl), and un-reacted $K_2CO_3$, as well as other impurities which include the diacid by-product hydroxy phthalic anhydride (OHPA), and small amounts of the partially hydrolyzed ODPA product (e.g. the diacid-mono-anhydride of ODPA (ODDA)) and the fully hydrolyzed ODPA product tetraacid (e.g. ODTA). Further, the temperature of the reaction product mixture is taken to be about 150° C. or higher, a temperature typical of chloro displacement reactions. For the purposes of the present prophetic examples, the reaction product mixture comprises the components and in the concentrations (by weight) shown in Table 3. The reaction product mixture described in Table 3 serves as an embodiment of the "first mixture" referred to in the claimed method of the invention (See for example, originally filed claim 1).

TABLE 3

Typical Crude ODPA Reaction Product Mixture

| Component | Wt % |
|---|---|
| ODCB | 65.0 |
| ODPA | 20.0 |
| KCl | 10.0 |
| ClPA | 2.0 |
| K2CO3 | 1.0 |
| HEG-Cl | 1.0 |
| ODTA | <0.5 |
| ODDA | <0.5 |
| OHPA | <0.5 |

Prophetic Example 1

Acid Treatment #1: The reaction product mixture is cooled (See explanation above) from about 150° C., down to a temperature of about 80° C. The ODPA crystallizes from solution as it cools. The reaction mixture is then contacted with an aqueous solution of an inorganic acid ($H_3PO_4$). The acid is used in an amount corresponding to about 1 molar equivalent of $H_3PO_4$ relative to the amount of ODPA present initially. The concentration of the inorganic acid in the aqueous solution is in a range of from about 2 to about 10 wt %. The temperature is most preferably in the range of 50-100° C.

By contacting the ODPA slurry with the aqueous acid solution, the ODPA hydrolyzes to ODTA. The method of contact between the acid solution and the crude reaction solution can be in batch mode and/or counter-current or co-current continuous mode. Agitation and/or other mixing techniques can be utilized to enhance mass transfer between the organic and aqueous phases. As the ODPA hydrolyzes to ODTA, it remains mostly as a solid phase, and the inorganic salts and HEGCl catalyst dissolve in the aqueous phase. The requisite time for contact of the two phases to ensure complete hydrolysis of ODPA to ODTA depends on the efficiency of mass transfer and the exact hydrolysis temperature employed within the above stated range.

Filtration/Centrifugation #1: After acid treatment is complete, the "third mixture" comprising an organic layer, an aqueous layer, and solid ODTA is cooled to a temperature which produces the maximum amount of solid ODTA without causing inorganic salts to crystallize from the aqueous phase. The cooled mixture is then subjected to a "filtration step" to separate the ODTA from the liquid phases. As noted, the term "filtration step" includes any process by which a solid dispersed in a liquid is separated from said liquid and includes separation by sintered metal filtration, rotary filtration, vacuum filtration, suction filtration, gravity filtration, decantation, centrifugation, or a combination of two or more of such techniques. The solid ODTA wet cake from obtained in the filtration step can also be washed with ODCB and water to remove any residual impurities that are entrained in the liquid trapped in the wet cake. The ODTA solids are then removed from the filter device as a wet cake. The wet cake is then dried to remove residual solvents or directly treated as a wet cake. The organic phase from the filtration contains non-hydrolyzed organic reactants, product or by-products as well as some small amount of catalyst. The aqueous filtrate contains the majority of the inorganic salts; the acid added to the system in the previous step, and the remaining HEGCl and hydrolyzed soluble organics.

Prophetic Example 2

Acid Treatment #2: The ODTA solids from Prophetic Example 1 are then treated with additional aqueous inorganic acid to remove any remaining impurities, including KCl, $K_2CO_3$, HEGCl and hydrolyzed organic impurities, for example chlorophthalic acid (ClDA) and OHDA. In this Prophetic Example, the amount of inorganic acid relative to ODTA is about 1 mole of acid per mole of ODTA. The acid treatment can be done at temperatures above the freezing point of the acid solution, and can also be done at elevated temperatures under pressure. After acid treatment is completed, the mixture is cooled to maximize the precipitation of ODTA in the aqueous slurry.

Filtration/Centrifugation #2: The solid ODTA from acid treatment #2 is then isolated in a filtration step. The ODTA is washed with water or other suitable solvent to displace any entrained acid solution. The wet cake from this process gives the purified ODTA, which can be thermally dehydrated to purified ODPA, by removal of water from the ODTA.

Prophetic Example 3

The reaction product mixture is cooled to about 80° C. and treated as in Prophetic Example 1 to provide a "third mixture" comprising an organic layer, an aqueous layer, and solid ODTA.

Phase Separation: After acid treatment, the third mixture is separated into aqueous and organic phases. The aqueous phase is lighter than the organic phase and separates in a layer on top of the organic phase. The ODTA solids are heavier than the aqueous phase and tend to be dispersed as a solid in the organic phase. (Because the ODTA is largely insoluble in the organic solvent, the organic phase is a slurry of solid ODTA and the organic solvent. The aqueous phase contains the majority of the inorganic salts and the HEGCl, as well as the inorganic acid. Water soluble organics (e.g. hydrolyzed organics such as chlorophthalic acid) are also comprised in the aqueous phase. The organic phase contains a very small amount of HEGCl, unhydrolyzed organics and solid ODTA. Phase separation of the organic slurry from the lighter aqueous layer is affected by decantation in a variety of ways known to those skilled in the art. The aqueous layer is taken off as a waste, and the organic phase, a slurry comprising the organic solvent and solid ODTA, is the purified tetraacid product.

ODTA Filtration, Dehydration & ODPA Isolation or Dehydration & ODPA Isolation: The organic phase is then subjected to a "filtration step" to produce a ODTA wet cake comprising ODTA and residual organic solvent. The ODTA is then washed with water or other suitable solvent to displace any entrained acid solution. The wet cake from this process is then the purified ODTA, which can be thermally dehydrated to purified ODPA, by removal of water from the ODTA.

Alternatively, the ODTA/organic slurry from above can be directly treated to thermally dehydrate the ODTA to ODPA, by heating and removing water from the mixture, until all the ODTA is converted to ODPA. At this point the ODPA solution and/or slurry is the purified product. If desired the solution/slurry can be cooled and the ODPA crystallized from the organic solution. The crystallized ODPA can then be separated from the organic solution by filtration/centrifugation in a method similar to those previously described.

Prophetic Example 4

Solvent evaporation: The reaction product mixture is transferred to a dryer system capable of removing the solvent, for example by distilling or otherwise evaporating. The dryer can be a rotary drum type, a dryer/filter type or any other type that is capable of removing the solvent from the reaction product mixture. The reaction product mixture is heated in the dryer and solvent is taken off. In addition vacuum distillation may also be used to effect solvent removal. Once the solvent is removed, the solid residue remaining comprises the ODPA product, the inorganic salts, the HEGCl phase transfer catalyst and un-reacted organics. Some volatile organic reactants can also be present in the evaporated solvent. The key is to remove a sufficient amount of the solvent to avoid the formation of a separate organic liquid phase in subsequent treatment steps.

Acid Treatment: The solids from the solvent evaporation step are then contacted with an aqueous acid solution in a manner similar to that described above in Prophetic Example 1 to provide an aqueous slurry of the tetraacid.

Filtration/Centrifugation: After acid treatment is complete, the aqueous slurry of the tetraacid (solid ODTA) is cooled to a temperature where the ODTA solid formation is maximized without causing inorganic salts to crystallize from the aqueous phase. The cooled mixture is then subjected to a filtration step to recover the solid ODTA. The solid ODTA wet cake is also washed with water to remove any residual impurities and acid that are entrained in the liquid trapped in the wet cake. The ODTA solids are then removed from the filter device as a wet cake. The wet cake can then be dried to remove residual solvents or used directly as a purified wet cake ODTA product. The aqueous filtrate contains the majority of the inorganic salts; the inorganic acid, HEGCl, and other water-soluble organics.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of preparing a purified dianhydride, said method comprising:
   (a) providing a first mixture comprising: an organic solvent, a dianhydride, and at least 10,000 parts per million of a metal halide salt relative to the total weight of the dianhydride;
   (b) combining the first mixture with water and at least one inorganic acid to form a second mixture;
   (c) heating said second mixture until substantially all of said dianhydride is converted to a tetraacid formed as an ingredient in a third mixture, said third mixture comprising an organic layer and an aqueous layer;
   (d) subjecting the third mixture to at least one operation selected from the group consisting of:
      (i) removing substantially all of the organic solvent to produce an aqueous slurry of the tetraacid;
      (ii) removing the organic layer from the aqueous layer to form a mixture comprising the tetraacid and the organic solvent; and
      (iii) filtering to form a tetraacid wet cake; and
   (e) subjecting the product formed in step (d) to at least one operation selected from the group consisting of:
      (iv) filtering to provide a tetraacid wet cake;
      (v) combining a tetraacid wet cake with at least one organic solvent to produce a mixture comprising a tetraacid and an organic solvent; and
      (vi) effecting ring closure of a tetraacid ingredient; to provide a purified dianhydride comprising less than 50 parts per million of said metal halide salt.

2. The method according to claim 1 wherein said organic solvent of the first mixture comprises at least one component selected from the group consisting of alcohols, ketones, amides, aromatic solvents, and ethers.

3. The method according to claim 2 wherein said organic solvent comprises orthodichlorobenzene.

4. The method according to claim 1 wherein said dianhydride is selected from the group consisting of dianhydrides having structure I

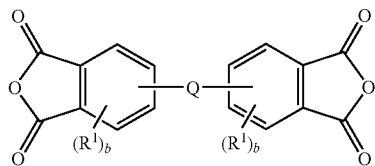

wherein Q is a bond, an oxygen atom, a sulfur atom, a sulfinyl group, a sulfonyl group, a selenium atom, a hexafluoroisopropylidene group, a $C_1$-$C_{30}$ aliphatic radical, a $C_3$-$C_{30}$ cycloaliphatic radical, or a $C_3$-$C_{30}$ aromatic radical, or a carbonyl group; $R^1$ is a halogen atom, a nitro group, a cyano group, a $C_1$-$C_{12}$ aliphatic radical, $C_3$-$C_{12}$ cycloaliphatic radical, or a $C_3$-$C_{12}$ aromatic radical;
   and b is independently at each occurrence an integer from 0 to 3.

5. The method according to claim 4 wherein said dianhydride is selected from the group consisting of oxydiphthalic anhydride; thiodiphthalic anhydride; sulfinyldiphthalic anhydride; sulfonyldiphthalic anhydride; carbonyldiphthalic anhydride; bisphenol A bisphthalic anhydride; hexafluoroisopropylidene bisphthalic anhydride; and biphenyldianhydride.

6. The method according to claim 1 wherein said inorganic acid comprises at least one acid selected from the group consisting of carbonic acid, boric acid, phosphoric acid, phosphorous acid, hydrochloric acid, sulfuric acid, sulfurous acid, and hydrobromic acid.

7. The method according to claim 1 wherein said inorganic acid comprises at least one acid selected from the group consisting of carbonic acid, and phosphoric acid.

8. The method according to claim 1 wherein said inorganic acid consists essentially of carbonic acid.

9. The method according to claim 1 wherein said inorganic acid consists essentially of phosphoric acid.

10. The method according to claim 1 wherein said inorganic acid consists essentially of hydrochloric acid.

11. The method according to claim 1 wherein the first mixture further comprises a phase transfer catalyst.

12. The method according to claim 11 wherein the phase transfer catalyst is selected from the group consisting of guanidinium salts, aminopyridinium salts, phosphazenium salts, and mixtures thereof.

13. The method according to claim 1 wherein said heating comprises heating at a temperature in a range between about 60° C. and about 160° C.

14. The method according to claim 1 wherein said heating is carried out at supratmospheric pressure.

15. A method of preparing a purified dianhydride, said method comprising:
   (a) providing a first mixture comprising: an organic solvent, a dianhydride, and at least 10,000 parts per million of a metal halide salt relative to the weight of the dianhydride;
   (b) filtering the first mixture to form a first mixture as a solid mass comprising the dianhydride, the metal halide salt, and residual organic solvent;
   (c) combining the first mixture with water and at least one inorganic acid to form a second mixture;
   (d) heating said second mixture until substantially all of said dianhydride is converted to a tetraacid formed as an ingredient in a third mixture;
   (e) subjecting the third mixture to the following operations:
      (i) removing substantially all of the residual organic solvent to produce an aqueous slurry of the tetraacid;
      (ii) filtering to form a tetraacid wet cake,
      (iii) combining the tetraacid wet cake with at least one organic solvent to produce a fourth mixture comprising the tetraacid and a solvent; and
      (iv) effecting ring closure in said tetraacid ingredient of the fourth mixture; to provide a purified dianhydride comprising less than 50 parts per million of said metal halide salt.

16. The method according to claim 15 wherein said inorganic acid comprises at least one acid selected from the group consisting of carbonic acid, boric acid, phosphoric acid, phosphorous acid, hydrochloric acid, sulfuric acid, sulfurous acid, and hydrobromic acid.

17. A method of preparing a purified oxydiphthalic anhydride, said method comprising:
(a) providing a first mixture comprising: an organic solvent, an oxydiphthalic anhydride, and at least 10,000 parts per million of a metal halide salt relative to the total weight of the oxydiphthalic anhydride;
(b) combining the first mixture with water and at least one inorganic acid to form a second mixture;
(c) heating said second mixture until substantially all of said oxydiphthalic anhydride is converted to a tetraacid formed as an ingredient in a third mixture, said third mixture comprising an organic layer and an aqueous layer;
(d) subjecting the third mixture to at least one operation selected from the group consisting of:
(i) removing substantially all of the organic solvent to produce an aqueous slurry of the tetraacid;
(ii) removing the organic layer from the aqueous layer to form a mixture comprising the tetraacid and the organic solvent; and
(iii) filtering to form a tetraacid wet cake; and
(e) subjecting the product formed in step (d) to at least one operation selected from the group consisting of:
(iv) filtering to form a tetraacid wet cake;
(v) combining a tetraacid wet cake with at least one organic solvent to produce a mixture comprising a tetraacid and an organic solvent; and
(vi) effecting ring closure in said tetraacid ingredient of a mixture comprising a tetraacid and an organic solvent;
to provide a purified oxydiphthalic anhydride comprising less than 50 parts per million of said metal halide salt.

18. The method according to claim 17 wherein said oxydiphthalic anhyrdide is selected from the group consisting of 3,3'-oxydiphthalic anhydride, 3,4'-oxydiphthalic anhydride, 4,4'-oxydiphthalic anhydride, and mixtures thereof.

19. The method according to claim 17 wherein said inorganic acid comprises at least one acid selected from the group consisting of carbonic acid, boric acid, phosphoric acid, phosphorous acid, hydrochloric acid, sulfuric acid, sulfurous acid, and hydrobromic acid.

20. The method according to claim 17 wherein said solvent is orthodichlorobenzene.

21. A method of preparing a purified dianhydride, said method comprising:
(a) providing a first mixture comprising: an organic solvent, a dianhydride, and at least 10,000 parts per million of a metal halide salt relative to the total weight of the dianhydride;
(b) combining the first mixture with water and at least one inorganic acid to form a second mixture;
(c) heating said second mixture until substantially all of said dianhydride is converted to a tetraacid formed as an ingredient in a third mixture, said third mixture comprising an organic layer and an aqueous layer;
(d) subjecting the third mixture to at least one operation selected from the group consisting of:
(i) removing substantially all of the organic solvent to produce an aqueous slurry of the tetraacid;
(ii) removing the organic layer from the aqueous layer to form a mixture comprising the tetraacid and the organic solvent; and
(iii) filtering to form a tetraacid wet cake; and
(e) subjecting the product formed in step (d) to at least one operation selected from the group consisting of:
(iv) filtering to provide a tetraacid wet cake;
(v) combining a tetraacid wet cake with at least one organic solvent to produce a mixture comprising a tetraacid and an organic solvent; and
(vi) effecting ring closure in said tetraacid ingredient of a mixture comprising a tetraacid and an organic solvent;
to provide a purified dianhydride comprising less than 50 parts per million of said metal halide salt.

* * * * *